United States Patent
Bass et al.

[11] Patent Number: 5,935,524
[45] Date of Patent: Aug. 10, 1999

[54] HOLDER FOR FLUOROMETRIC SAMPLES

[75] Inventors: Jay Kevin Bass, Hockessin, Del.; David James Regester, West Grove, Pa.

[73] Assignee: E. I. du Pont de Nemours and Company, Wilmington, Del.

[21] Appl. No.: 08/844,742

[22] Filed: Apr. 21, 1997

Related U.S. Application Data

[60] Provisional application No. 60/016,758, May 7, 1996, abandoned.

[51] Int. Cl.[6] .............................. B01L 9/00; G01N 21/64
[52] U.S. Cl. .............................. 422/104; 422/52; 422/55; 422/58; 422/82.05; 422/102
[58] Field of Search .................... 422/50, 52, 55, 422/58, 82.05, 102, 103, 104

[56] References Cited

U.S. PATENT DOCUMENTS

| | | |
|---|---|---|
| 3,992,631 | 11/1976 | Harte ........................................ 250/365 |
| 5,035,861 | 7/1991 | Grandone .................................... 422/64 |
| 5,139,745 | 8/1992 | Barr et al. ................................ 422/82.5 |
| 5,544,683 | 8/1996 | Guhl .......................................... 141/65 |
| 5,637,469 | 6/1997 | Wilding et al. ......................... 435/7.21 |

FOREIGN PATENT DOCUMENTS

| | | | |
|---|---|---|---|
| 0 181 291 A2 | 5/1986 | European Pat. Off. | ....... G01N 21/03 |
| 0580362 A1 | 7/1993 | European Pat. Off. | . |
| 0 580 362 A1 | 1/1994 | European Pat. Off. | ....... G01N 21/64 |
| 3108474 A1 | 9/1982 | Germany | ........................ G01N 21/01 |
| 4214161 A1 | 11/1993 | Germany | ........................ G01N 21/13 |
| 95/00832 | 1/1995 | WIPO | .............................. G01N 21/64 |

*Primary Examiner*—Harold Y. Pyon

[57] ABSTRACT

A holder for fluorometric analysis of PCR reaction tubes comprises a longitudinal block, the block being sized to fit within a fluorometer; a cavity disposed along a longitudinal axis of the block; at least one test well within the cavity, the test well having an internal wall sized to closely receive and maintain intimate contact with a substantial portion of a single PCR reaction tube therein; the internal wall having at least one optical port therein; and a cover movably connected to the block.

5 Claims, 3 Drawing Sheets

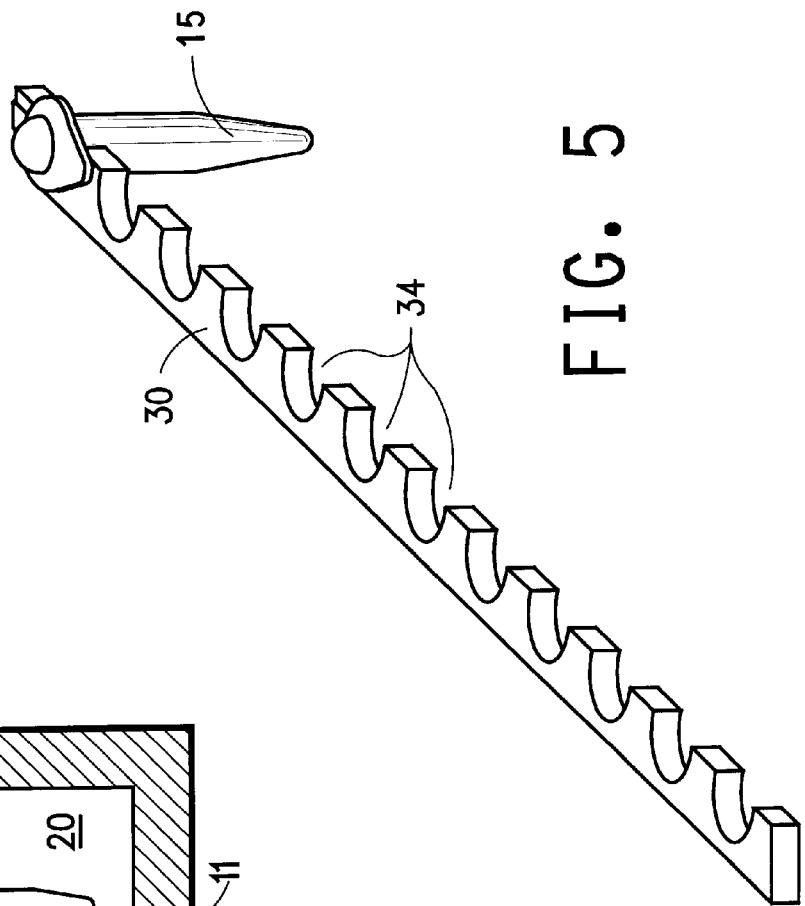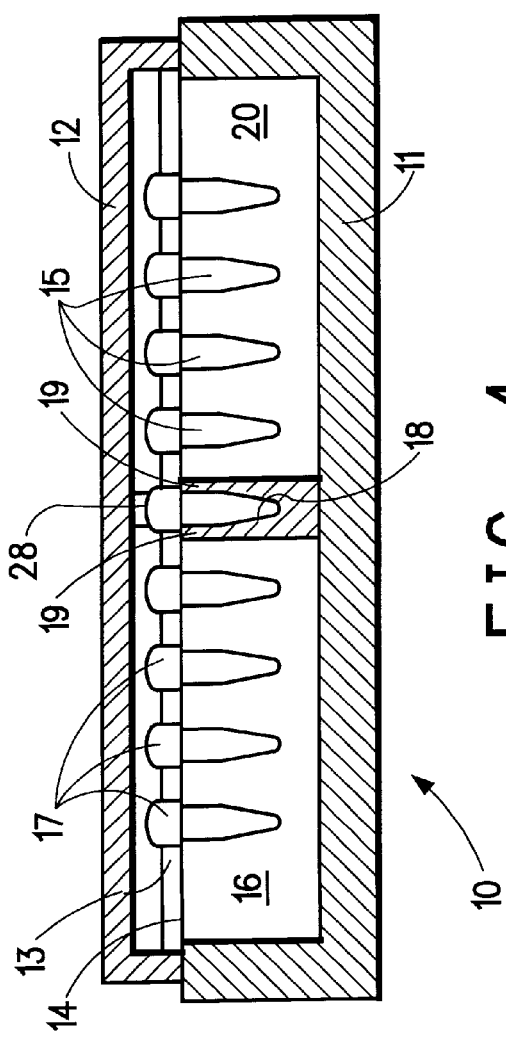

HOLDER FOR FLUOROMETRIC SAMPLES

This application claims priority benefit under 35 U.S.C. 119(e) from U.S. Provisional application No. 60/016,758 filed May 7, 1996, now abandoned.

BACKGROUND OF THE INVENTION

This invention relates to instrumentation for fluorometric analysis of polymerase chain reaction (PCR) samples wherein the amplified product is bound to an intercalating fluorescent dye and more particularly to a holder which provides rapid and convenient manual progression of reaction strips used as cuvettes in a fluorometer.

Polymerase chain reaction ("PCR") is a powerful analytical tool which has become increasingly popular and useful in a variety of applications, from matching bodily fluid samples to a defendant in criminal procedures to identifying unknown organisms in a biological or environmental sample. PCR is an assay which amplifies a desired specific nucleic acid fragment or sequence contained in a nucleic acid or mixture of nucleic acids. The PCR assay is based on a protocol of thermal incubation in which the sample is subjected to a repeated sequence of alternating elevated temperatures for controlled time periods. Higher and lower temperature incubations are alternated in a repeated sequence or cycle, and the cycle is then repeated for a specified number of times.

Following PCR, existence of an amplified product must be determined. There are a number of known methods. The most common involves gel electrophoresis in which wells associated with individual lanes are charged by pipette with a sample or a control. An electrical potential is applied across the wells causing DNA fragments to migrate at rates proportional to size and electrical charge. After separation, the gel is stained as with ethidium bromide, which fluoresces when properly excited, and read.

Another method involves capturing or immobilizing reaction products in a 96-well microtiter plate, commercially available from ICN Titertek and read on a commercial plate reader such as the Fluoroskan, also available from ICN Titertek. A modified 96-well plate with tapered cavities ("V-bottom") specifically sized for the tubes used in the Perkin Elmer cycler is available from Evergreen. This fits into a plate reader such as the Fluoroskan.

Still another technique, disclosed in Canadian Patent Application 2,067,909, uses a DNA binding agent which provides a detectable signal when bound to double-stranded nucleic acid which signal is distinguishable from the signal when it is unbound. The technique employs an intercalating agent, such as a fluorescent dye (e.g., ethidium bromide) and a spectra fluorometer in conjunction with optical fibers.

These above procedures and techniques have several disadvantages. First, any technique which requires the sample to be transferred, such as by pipette, to another container or surface presents the possibility of contamination. In addition, samples must be prepared in a isolated room or hood to avoid contamination from the room where the tubes are opened. Accordingly, it is preferred that the sample be "read" in its original container. Second, the large 96-well plates, while adequate for large numbers of samples, are often cumbersome and unwieldy when only a few samples need to be read. Third, reading of multiple well plates must be done from the top, removing the source of the signal from the sensor. Fourth, electrophoretic gels can be difficult to produce, handle and develop and suffer from several of the problems related above as well.

SUMMARY OF THE INVENTION

Briefly stated, the invention comprises a holder for fluorometric analysis of PCR reaction tubes, the holder comprising: a longitudinal block having at least one test well therein, the block being sized to fit within a fluorometer; a cavity disposed along a longitudinal axis of the block; at least one test well located within the cavity, the test well having an internal wall sized to closely receive and maintain intimate contact with a substantial portion of a single PCR reaction tube therein; the internal wall having at least one optical port therein; and a cover movably connected to the block.

During use of the preferred embodiment, a strip of PCR reaction tubes (e.g., an 8 or 12-tube strip) is inserted into the holder with an end tube of the strip in the test well and the other tubes in one of the two in-line longitudinal cavities. The cover is closed biasing the reaction tube in the test well into intimate contact with the internal walls thereof. The fluorometer reading is taken through the apertures in the internal wall of the test well (it being understood by those in the art that an appropriate dye has been introduced into the PCR reaction prior to amplification). The cover is then opened and the tubes indexed such that the next sample reaction tube in the strip is placed into the test well. The process is repeated until all tubes in the strip have been read fluorometrically. Tubes are not opened and neither a clean room or a hood is required.

BRIEF DESCRIPTION OF THE DRAWINGS

FIG. 4 is a sectioned elevational view of the holder of FIG. 3 shown containing a typical strip of PCR sample tubes therein, as seen along lines and arrows IV—IV of FIG. 3.

FIG. 5 is a perspective view of an adapter for use in connection with the holder of this invention.

DETAILED DESCRIPTION OF THE EMBODIMENTS

Figure 1:
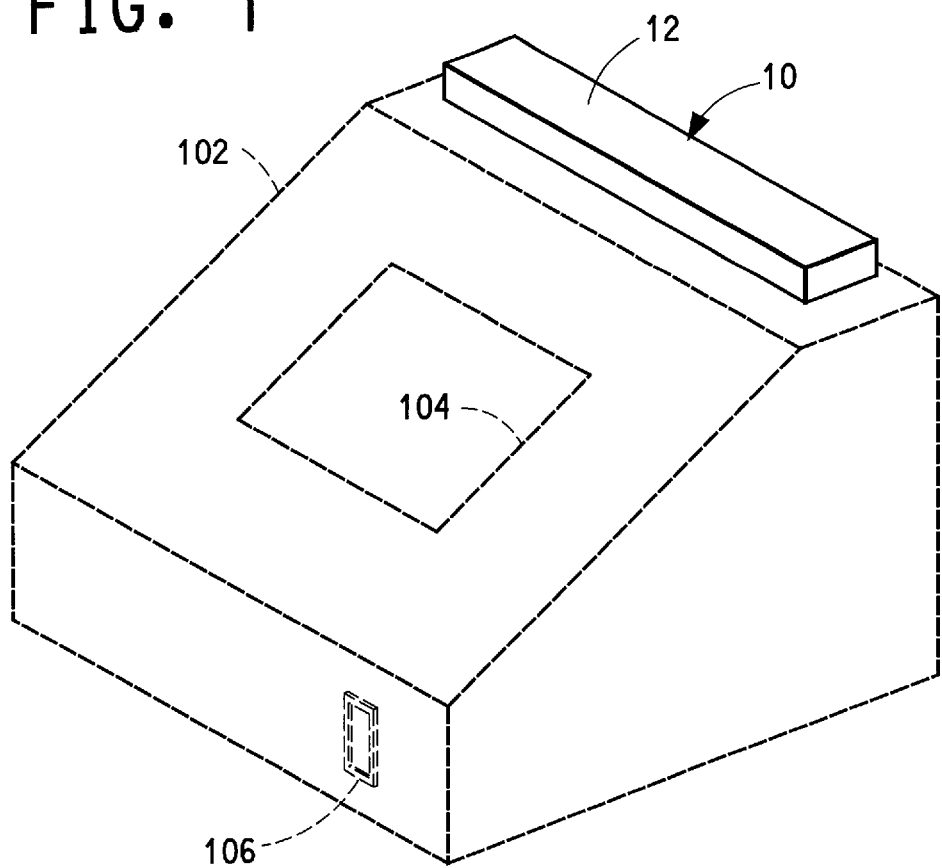
FIG. 1 is a perspective view of a typical fluorometer (in phantom) showing the holder of the invention inserted therein with the cover in closed position.

With reference being made to FIG. 1, a typical fluorometer is shown. Because the fluorometer shown is intended to be generic and not a specific illustration of a particular unit, it is being shown in broken lines. A typical fluorometer, as known to those skilled in the art, comprises an outer enclosure 102, a control and readout panel 104 and a power switch 106. The electronic and optical components of the fluorometer are located within the enclosure 102. The holder of this invention 10 is shown attached to the fluorometer with cover 12 of holder 10 closed.

Figure 2:
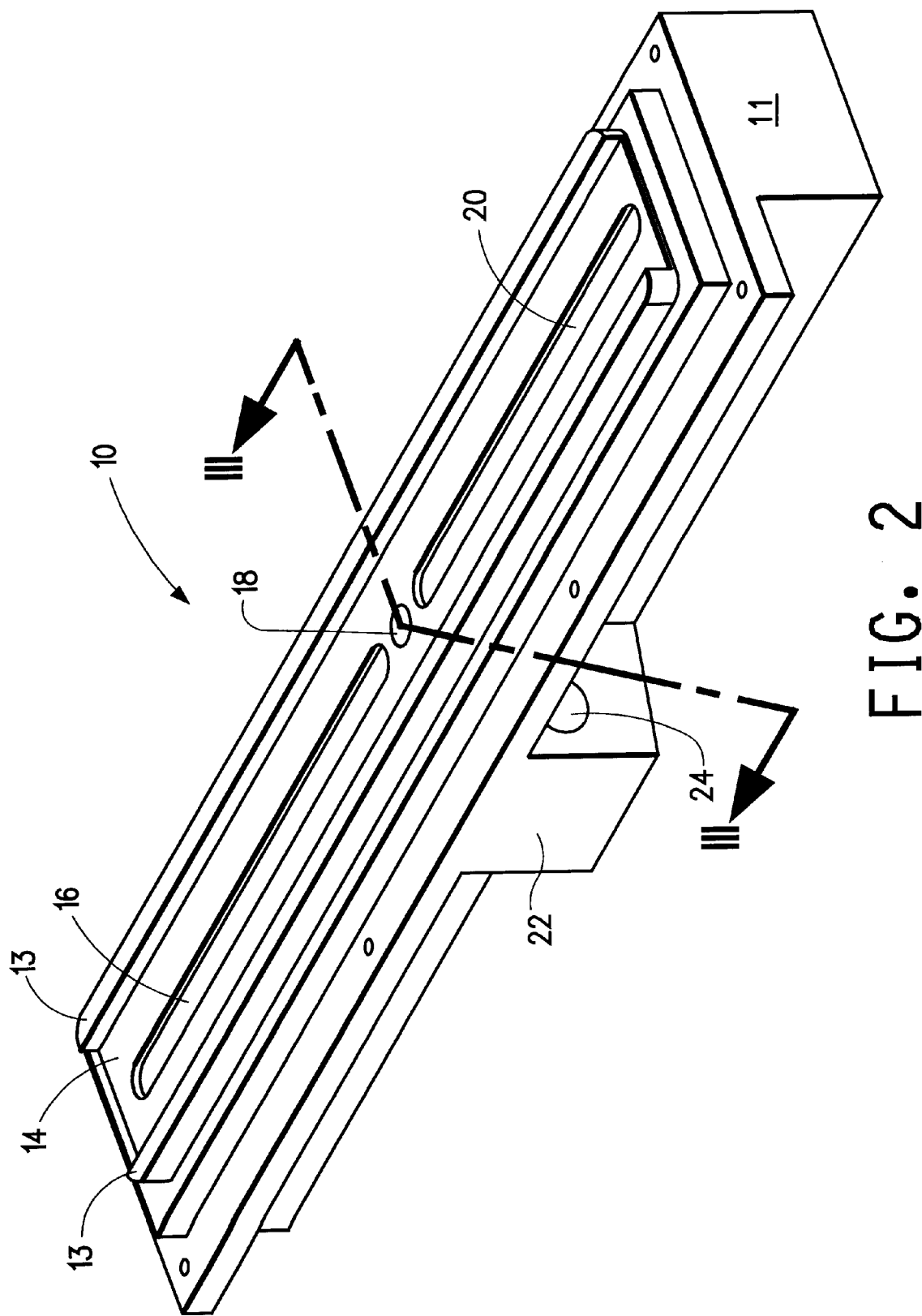
FIG. 2 is a perspective view of a preferred embodiment of the holder of the invention with its cover removed for ease of illustration.

With reference now being made to FIG. 2, holder 10 comprises a longitudinal block 11 having a test well 18 located therein. In the embodiment shown, the test well 18 is generally centrally located relative to the longitudinal block 11. Two longitudinal slot-like cavities 16, 20 are oriented in-line with one another, each cavity 16, 20 being disposed on opposite sides of test well 18. A web 19 separates each cavity 16, 20 from the test well 18. Holder 10 may be conveniently made of metals (e.g., aluminum) or any number of plastics or polymers by techniques (e.g., injection molding, stamping, milling) that are well known in the art. To reduce light scatter, it is preferred that the holder be a dark (e.g., black) color with a mat finish.

Integral with holder 10 and dependent therefrom is boss 22 which is pierced by two apertures 24 (only one of which is visible in the Figures) disposed normal to one another. The apertures 24 are sized to retain optical fibers, not shown, which are part of typical fluorometer. One of these apertures 24 (the excitation port) will hold the optical fiber that delivers the electromagnetic radiation to excite the material in the reaction tube. The other aperture 24 (the reading port) will hold the optical fiber that will read the electromagnetic radiation (i.e., fluorescence), if any, emanating from the reaction tube after excitation.

A pair of longitudinally oriented rails 13, 13 flank the test well 18, and the longitudinal cavities 16, 20. The rails 13, 13, together with the upper surface of the block 11, define a sliding surface 14 for the strip of PCR reaction tubes, as described more fully below. In the embodiment shown, rails 13, 13 serve as a light barrier as well as a friction hold for cover 12.

Figure 3:
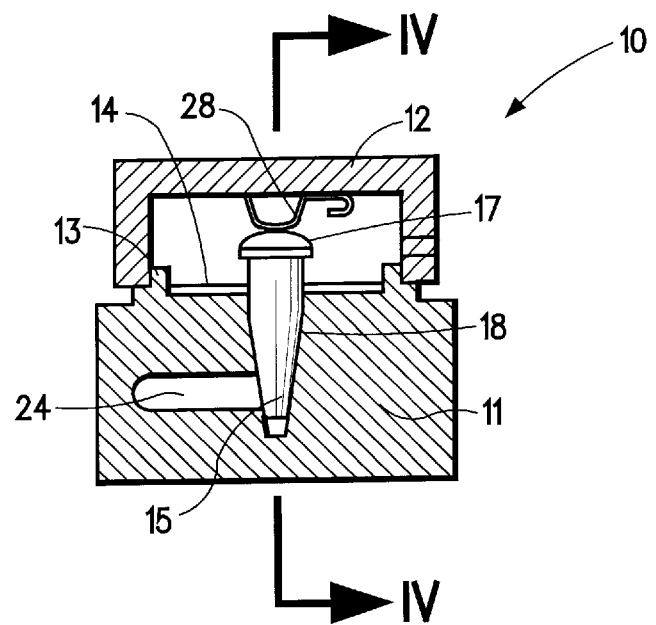
FIG. 3 is a cross-sectional view of the holder of FIG. 2 with the cover closed and a sample tube contained therein, as seen along lines and arrows III—III of FIG. 2.

Referring now to FIG. 3, test well 18 has an internal wall sized to closely receive and maintain intimate contact with a substantial portion of a PCR reaction tube 15 contained therein. In particular, the lower end of test well 18 is tapered to provide mating engagement between the PCR tube 15 and the internal wall of the test well 18. The position of apertures 24 (only one being shown) relative to the test well 18 is also shown in FIG. 3.

As seen in FIG. 3, holder 10 includes a cover 12, which, in the embodiment shown, is a substantially box shaped member. The cover 12 may be attached to block 11, such as by a hinge, for pivotal movement between open and closed positions or, alternately, may be a separate member that can be removably attached to the block 11. As also seen in FIG. 3, the cover 12 is provided with a biasing member, such as leaf spring 28, on its inner surface. The leaf spring 28 is positioned to make contact with the cap 17 of PCR reaction tube 15 when the cover 12 is closed. In this manner, leaf spring 28 provides a downward biasing force on PCR tube 15 to bias same into intimate contact with the internal wall of the test well 18, and thus facilitate a proper fluorometric reading. As will be apparent from the above description, the cover 12 should provide a tight fit when in the closed position, which may conveniently be accomplished by providing cover 12 to fit in friction contact with rails 13, 13 as shown in FIG. 3. Other means of securing cover 12 in its closed position are also suitable.

Referring now to FIG. 4, cavities 16, 20 are sized to hold the PCR reaction tubes 15 in the strip of PCR tubes. As mentioned above, these strips typically are sold in strips of 8 or 12 PCR tubes in spaced relation to one another. Preferably, the cavities 16, 20 are long enough to accommodate 12 PCR tubes. We prefer to hold one extra tube in case we wish to leave the strip in the fluorometer without having one of the tubes under constant excitation. The cavities 16, 20 should also be deep enough that the PCR tubes 15 are fully therein and do not bottom out in the cavities. The width of the cavities 16, 20 should be such that the tubes 15 fit therein in sliding relation and are suspended by the sliding surface 14. The web 19 of material separating the test well 18 from cavities 16, 20 is sized to match the distance between adjacent tubes 15 in the tube strip.

In use, a strip of tubes 15, with caps 17 in place, are removed from the thermal cycler used in the PCR protocol and are inserted into one of cavities 16 or 20, with the first tube in the strip being placed in the test well 18. The cover 12 is closed, biasing the tube 15 in the test well 18 into intimate contact with the walls. The fluorometer reading is taken, the cover 12 opened and the strip of tubes 15 is advanced one tube, whereby the next tube is placed into the test well 18. The first tube in the strip, that is the tube already read fluorometrically, is placed in the cavity (either 16 or 20) that is not occupied by the remaining tubes in the tube strip. The process is then repeated until all tubes in the strip have been fluorometrically read.

With reference now being made to FIG. 5, an adapter 30 is provided for use in connection with the holder of the invention. In particular, adapter 30 comprises a substantially planar elongate member having a plurality of semi-circular notches 34 spaced along one longitudinal edge thereof. The notches 34 are adapted to hold PCR reaction tube 15 therein, as shown. It is to be understood that notches 34 could readily be replaced by circular or other suitably shaped apertures. Adapter 30 can thus be used for an individual PCR tube or a strip of PCR reaction tubes. It is particularly preferred that adapter 30 be sized to slide between rails 13, 13.

In yet another embodiment, the adapter 30 may be permanently mounted for sliding movement between rails 13, 13. In this embodiment, manual or mechanical means may be employed to advance adapter 30 one tube at a time into well 18. In such an embodiment, a suitable passageway would need to be provided in block 11 to permit the PCR tubes 15 to be slid through the block as the adapter 30 is advanced. It will be apparent to those skilled in the art that this embodiment offers the advantage that the fluorometric analysis of the PCR tubes can be automated (or semi-automated) and the tubes can be advanced and analyzed without having to open the cover 12.

While the above description has been limited to the preferred embodiment shown, it is to be understood that the invention is not so limited. In particular, the embodiment shown and described above utilizes two optical fibers. It will be apparent to those skilled in the art that the invention may be used with a single fiber system, wherein a single fiber both carriers the excitation energy and returns the fluorescent energy. Such fibers are known where the single fiber is bifurcated towards its point of origin (into, for example a core and outer ring) to split the incoming and outgoing energy. The ends of the bifurcated single fiber would then be connected to the excitation source or the fluorescence sensor as appropriate. In addition, the embodiment shown and described employ a single test well and move the individual PCR tubes into that well for fluorometric analysis. Those skilled in the art will recognize that the invention is equally applicable to uses where the PCR tubes are placed in a series of testing wells, complete with optical excitation and sensing components. In such an embodiment, the tubes would remain stationary and each individual tube would be excited and the fluorescence measured seriatim.

What is claimed is:

1. A holder for fluorometric analysis of PCR reaction tubes, the holder comprising: a longitudinal block having at least one test well therein, said block being sized to fit within a fluorometer; a longitudinal cavity disposed along a longitudinal axis of the block; at least one test well generally centrally located within the longitudinal cavity, said test well having an internal wall sized to closely receive and maintain intimate contact with a substantial portion of a single PCR reaction tube therein; said internal wall having at least one optical port herein; and a cover movably connected to said block.

2. The holder of claim 1, wherein said cover comprises means for biasing a PCR tube into intimate contact with the internal wall of said at least one test well.

3. The holder of claim 2, wherein said biasing means comprises a spring affixed to an inner surface of said cover.

4. The holder of claim 1, wherein said at least one optical port comprises an aperture in said internal wall adapted to receive and hold an optical fiber therein.

5. The holder of claim 1, further comprising a pair of longitudinal rails positioned one on either side of the test well and the longitudinal cavity, said rails, together with an upper surface of the block defining a sliding surface for a strip of PCR reaction tubes and wherein said rails comprise a light barrier and a friction seal for the cover.

* * * * *